United States Patent [19]

Murray et al.

[11] 4,307,071

[45] Dec. 22, 1981

[54] ANALYTICAL REAGENT AND METHOD

[75] Inventors: Dennis M. Murray, Golden Valley; John W. Rosevear, Edina; Dan C. Drinkwitz, Minneapolis, all of Minn.

[73] Assignee: Kallestad Laboratories, Inc., Chaska, Minn.

[21] Appl. No.: 821,078

[22] Filed: Aug. 2, 1977
(Under 37 CFR 1.47)

[51] Int. Cl.$^2$ ............ G01N 33/16; A61K 43/00; C07G 7/00
[52] U.S. Cl. ............ 424/1; 23/230 B; 260/112 B; 424/12
[58] Field of Search ............ 424/1, 115, 12; 23/230 B; 260/112 B

[56] References Cited

U.S. PATENT DOCUMENTS

| | | | |
|---|---|---|---|
| 2,957,808 | 10/1960 | Campbell | 424/12 |
| 3,911,096 | 10/1975 | Chopra | 424/1 |
| 3,928,553 | 12/1975 | Hollander | 424/1 |
| 3,951,748 | 4/1976 | Devlin | 424/12 |
| 3,995,019 | 11/1976 | Jerome | 424/1.5 |
| 4,018,883 | 4/1977 | Parslow | 424/1 |
| 4,021,534 | 5/1977 | Lafontaine | 424/1 |
| 4,034,073 | 7/1977 | Weetall | 424/1 |
| 4,069,352 | 1/1978 | Parsons, Jr. | 424/1 |

OTHER PUBLICATIONS

Hales, et al., Biochem. J., 83, 1963, pp. 137–146.
Eckert, Angewandt Chemie, vol. 15, No. 9, Sep. 1976, pp. 525–533.
Siegel et al., J. Clin. Endocrinology Met., 37, 1973, pp. 526–532.

Primary Examiner—Benjamin R. Padgett
Assistant Examiner—Christine M. Nucker
Attorney, Agent, or Firm—James R. Haller

[57] ABSTRACT

A reagent is disclosed for determining the concentration of a ligand in blood serum. The reagent includes a protenaceous, three-dimensional, serum-insoluble complex which is readily collected by centrifugation, the complex comprising non-specific immunoglobulins, anti-ligand immunoglobulins, immunoglobulins which are antibodies to the previously mentioned immunoglobulins and which are complexed therewith, and a labeled ligand complexed with the anti-ligand immunoglobulins. The reagent is particularly useful in competitive binding analyses such as radioimmunoassays.

17 Claims, No Drawings

ANALYTICAL REAGENT AND METHOD

BACKGROUND OF THE INVENTION

The measurement of concentrations of such ligands as thyroid hormones in human blood serum is widely accepted as an important diagnostic aid in identifying particular functional disorders. For example, knowledge of the concentrations of thyroxine ($T_4$) and triiodothyronine ($T_3$) in human serum is of great usefulness to a diagnostician. Other ligands which lend themselves to quantitative analysis via radioimmunoassay include insulin, digoxin, and human growth hormone, and reference is made to the rather exhaustive treatise by Dr. Hans Georg Eckert reported in *Angewandte Chemie*, Volume 15, No. 9, September, 1976 at pages 525–533 for a non-exclusive list of ligands for which radioimmunoassay processes are feasible. Analyses by radioimmunoassay are particularly valuable for ligands having concentrations in blood serum at the nanogram to picogram per ml levels.

Broadly speaking, the radioimmunoassay procedure involves the use of an antibody which is specific to the ligand to be measured, and also a radioisotopically labeled ligand to which the antibody is also specific. The ligand to be measured and the labeled ligand compete for antibody binding sites. Eventually a measurable state is reached at which the relative concentrations of labeled and unlabeled ligands complexed or bound to the antibody are dependent upon the relative concentrations of the labeled and unlabeled ligands available and competing for the antibody binding sites. Since the amount of labeled ligand is constant, the amount of antibody-complexed labeled ligand will vary inversely with the amount of unlabeled ligand available and competing for the antibody binding sites. Folowing a suitable separation procedure, the amount of labeled ligand which remains bound to the antibody is indicated by radioisotope counting procedures (e.g., through the use of a gamma counter). The thus-indicated concentration of labeled ligand is compared with results from a number of control analyses involving samples having known concentrations of the ligand to be determined to infer the concentration of the unlabeled ligand.

Simplicity, accuracy, and reproducibility of radioimmunoassays or other assays involving competitive binding of labeled and unlabeled ligands to antibodies are highly desired features which contribute to the usefulness of such analyses in medical laboratories. It is evident that accuracy ordinarily decreases and the chances for error increase with the number of separate steps which must be taken in analyses of this type. To this end, it is preferable that few reagents (ideally, but a single reagent) be employed in such analyses, and that the time required to reach the desired degree of equilibration between the labeled and unlabeled ligand complexed with an antibody be as short as possible. Since, with some exceptions, equilibrium is approached more rapidly at increased temperatures, it is desired that the reagent or reagents be stable at relatively high temperatures. Further, it is necessary to isolate or separate the ligand-complexed antibody from the uncomplexed ligand during the assay procedure. It is important from the standpoint of accuracy that the separation procedure be carried out completely and reproducibly. When separation is performed by precipitation of the antibody-ligand complex, essentially none of the precipitate should be lost in the process, nor should the supernatant remain with the precipitate in any significant quantity.

Typical radioimmunoassay methods for thyroxine and triiodothyronine are taught in U.S. Pat. Nos. 3,911,096 and 3,928,553. The former patent describes a radioimmunoassay procedure for, for example, $T_4$, which involves first incubating, for an hour, human serum to be tested in the presence of an anti-$T_4$ antibody, radioisotopically labeled $T_4$, and a "blocking agent" which prevents the binding of $T_4$ to such blood proteins as thyroxine-binding globulin. The antibody, with its complexed $T_4$ moieties, is then separated as, for example, by addition of a second antibody such as goat anti-rabbit gammaglobulin, which then causes precipitation. The latter patent contains similar teachings.

SUMMARY OF THE INVENTION

The invention relates to a reagent for determining the concentration of a ligand such as $T_4$ or the like in blood serum. The reagent comprises a proteinaceous, three-dimensional, seruminsoluble complex which, broadly, includes non-specific immunoglobulins, anti-ligand immunoglobulins complexed with a labeled (e.g. radioisotopically labeled) ligand, and immunoglobulins which are antibodies to the previously mentioned immunoglobulins and which are complexed with them to form a three-dimensional lattice. The reagent may also include such adjuvants as may be necessary or desirable in the analyses of various ligands. For example, if the ligand to be analyzed is $T_4$, the reagent may include a binding inhibitory agent and may be controlled at a pH in the range of about 8-9 to allow formation of the $T_4$-antibody complex while preventing $T_4$ from binding to such serum proteins as thyroxine binding globulin (TBG), pre-albumin and albumin. The three-dimensional lattice forms an insoluble complex which is readily suspendable in the reagent for aliquoting, pipetting and mixing with the sample being analyzed.

The reagent, which thus include a variety of complexed immunoglobulins, is surprisingly stable at such unusually high temperatures as 50° C., or even 56° C., for periods of up to an hour or more. The reagent thus can be used at these temperatures to increase the rate at which substantial equilibrium is reaches in certain competitive binding assays such as radioimmunoassays for $T_4$, $T_3$, etc.

"Substantial equilibrium", as used herein, means that state at which the relative concentrations of antibody-bound labeled and unlabeled ligands are measurable and are dependent, within experimental error, upon the relative concentrations of such ligands present. This state may be either near or far from true chemical equilibrium, but must be measurable in that the concentrations of constituents must remain substantially constant within experimental error during the time of the measurement.

When substantial equilibrium has been reaches, the suspended three-dimensional complex is easily centrifuged to form a cohesive precipitate from which the supernanant can easily be decanted or aspirated.

In analyses for such ligands as $T_4$, $T_3$ and cortisol, the reagent of the invention is the only reagent which is needed for addition to a blood serum sample being analyzed. Of course, various other materials, such as serum standards, will be used to establish a calibration curve from which the result of the analyses may be read, as set forth more fully below.

The invention also relates to a method for use of the reagent of the invention, in which, broadly, predetermined quantities of a patient's blood serum and the reagent of the invention are measured into a test vessel such as a test tube, and the resulting mixture is incubated at a temperature of about 50° C. or above until substantial equilibrium is reached (usually not greater than one hour and preferably not greater than about 30 minutes). The test tube is centrifuged to separate the precipitate from the supernatant, and the concentration of ligand in the blood serum is determined by known means involving analysis of the precipitate or supernatant for the concentration of labeled ligand or a related quantity (such as radioactivity in radioimmunoassay analyses).

The invention further relates to a method for preparing the reagent of the invention, which comprises:

(a) providing immunoglobulins from a first animal species which are anti-ligand antibodies;

(b) providing immunoglobulins from a second animal species which are antibodies specific to immunoglobulins from the first animal species;

(c) providing non-specific immunoglobulins from the first animal species;

(d) reacting the non-specific immunoglobulins and the immunoglobulins from the second animal species to form an insoluble three-dimensional complex;

(e) thereafter reacting the immunoglobulins which are anti-ligand antibodies with the complex to provide the complex with a plurality of available ligand binding sites; and (f) thereafter reacting the complex with labeled ligand in sufficient quantity so that a significant fraction of the binding sites are complexed with the labeled ligand.

DESCRIPTION OF THE PREFERRED EMBODIMENTS

For brevity and ease of understanding, the invention is described below with respect to a reagent useful in the radioimmunoassay of thyroxine ($T_4$). It will be understood that the invention is applicable as well to various other ligands such as those described above and in the above-mentioned treatise of Dr. H. G. Eckert, which is incorporated herein by reference.

A basic feature of the invention involves the use, in a single liquid reagent system, of a large, complexed, three-dimensional proteinaceous complex which is easily separated by centrifugation but which is capable of being suspended in the liquid reagent as a water-insoluble suspension. The molecule includes antibody binding sites which, from an immunological standpoint, are anti-ligand (e.g., anti-$T_4$), with a substantial majority of the antibody binding sites being sterically unhindered and available for complexing with the ligand, and a significant fraction of the sites being occupied or complexed with labeled ligands. Except for the labeled ligands, the three-dimensional complex consists primarily of various immunoglobulins which are complexed with one another by chemical bonds normally associated with antigen-antibody bonding; e.g., hydrogen bonding or coordinate bonding. Despite the generally weak nature of the bonds thus described, the proteinaceous complex is surprisingly stable to temperatures in the 50°-60° C. range, e.g., the insolubility and the ligand-binding properties of the complex are substantially unchanged after exposure for 30 minutes to such temperature.

The general method of manufacture of the proteinaceous complex involves the use of a primary antibody raised in a first animal species and which is specific to the ligand to be analyzed, a secondary antibody raised in a different animal species against immunoglobulins of the first species; and non-specific immunoglobulins from the first species.

In one embodiment, a rabbit antiserum containing antibodies specific to a ligand such as $T_4$ is reacted in vitro with a complex of the secondary antibody and non-specific immunoglobulins. The secondary antibody may be provided by an antiserum raised in goats against rabbit immunoglobulins, and the non-specific immunoglobulins may be provided by normal rabbit serum. The quantities of the constituents are adjusted so that as much as possible of the primary antibody is brought down in the resulting precipitate. Non-precipitated material is washed away, leaving an insoluble three-dimensional complex consisting almost entirely of primary antibody, secondary antibody, and additional immunoglobulins. To a suspension of the complex is then added labeled ligand, e.g., radioactively labeled $T_4$ such as $^{125}I$-$T_4$. The resulting proteinaceous three-dimensional complex is employed in an aqueous carrier which includes a binding inhibitory agent such as 8-anilino-1-naphthalene sulphonic acid, and a buffering material such as a sodium borate buffer to maintain the pH above about 8, human serum albumin, $NaN_3$, and the disodium salt of ethylenediaminetetraacetic acid ($Na_2$ EDTA).

"Non-specific immunoglobulins", as used herein, refers to immunoglobulins from the first animal species which are antigens to antibodies of the second animal species but which are not antibodies specific to the ligand.

As thus described, the three-dimensional proteinaceous material complexed with the labeled ligand can easily be centrifuged from the remainder of the reagent to form a cohesive precipitate from which the supernatant can be removed with ease and without any significant disturbance of the precipitate.

The immunoglobulins described above can be raised in a number of laboratory animals by known methods, as generally laid out in *Methods in Immunology and Immunochemistry*, Volume I Williams and Chase, Eds, Academic Press, New York, 1967, pp. 197–306. For example, the primary anti-ligand antibody for such small molecules as $T_3$ and $T_4$ may be raised in rabbits by conjugating the $T_3$ or $T_4$ to a large molecule such as albumin, repeatedly injecting several rabbits with this material, and determining by test bleedings and titrations which of the animals is producing an acceptably high quantity of antibodies specific for $T_3$ or $T_4$. The secondary antibody may be raised in goats by similar procedures involving injections of the goats with rabbit immunoglobulins. The non-specific immunoglobulin constituent may be immunoglobulins from normal rabbit serum as representative of immunoglobulins from the species in which the anti-ligand antibodies were raised.

One procedure for producing the large, complex, proteinaceous material from the above-described constituents involves combining normal rabbit serum (containing, among other constituents, non-specific immunoglobulins) and the secondary antibody (the goat antibody to rabbit immunoglobulin) in a ratio such that the latter ingredient is present in at least an amount effecting substantially complete precipitation of the immunoglobulins in the normal rabbit serum. The ratio is selected on the basis of preliminary titering determinations following known procedures. To this suspension is then added the rabbit antiserum containing antibodies to the ligand (e.g., $T_4$), to form a proteinaceous, three-dimensional complex which can be recovered by precipitation and which is then washed to remove substantially all non-precipitated materials. This material has a plurality of ligand complexing sites due to the incorporation of the anti-ligand antibody thereon. The relative amounts of the primary and secondary antibody ingredients and the normal rabbit serum are chosen such that, in an analysis of human blood serum for ligand concentration, a reasonably large quantity of precipitate is collected from each test, and such that when employing a small quantity, e.g., 20 microliters of human blood serum to be tested, the range of sensitivity of the assay is appropriate to diagnostic needs.

To the insoluble antibody complex thus prepared is added a labeled ligand (such as $^{125}I$-$T_4$) in a quantity such that a portion, e.g., about 50%, of the labeled ligand is bound to the anti-ligand antibody sites in the complex, the bound sites representing only a a portion of the total sites available for complexing with the ligand.

The quantity of labeled ligand to be used depends upon the effective ligand binding capacity of the complex; that is, upon the quantity of ligand which becomes actually bound to a given quantity of the complex. The effective binding capacity for the population of antibodies present can be determined, for example, by combining increasing known volumes of labeled ligand (e.g., $^{125}I$-$T_4$) with constant known volumes of the complex resulting from the preceding paragraph in a series of testtubes, permitting the resulting samples to closely approach quilibrium, centrifuging each sample to separate the precipitate, removing the supernatant (containing unbound labeled ligand) and measuring the quantity of bound labeled ligand in the precipitate. Of course, actual quantities of a ligand such as $^{125}I$-$T_4$ need not be measured; instead, relative quantities may be determined by counting procedures using a gamma counter. The effective binding capacity is indicated by noting the point at which further increases in the volume of added $^{125}I$-$T_4$ produce substantially no further increases in the quantity of bound $^{125}I$-$T_4$ in the precipitate. In the case of a particularly heterogeneous population of antibodies, the binding capacity can be estimated by plotting the data in the form of a Scatchard plot (see *Mathematical Theory of Radioimmunoassay*, Henry Feldman and David Rodbard, Chap. VI).

Also added is an inhibiting quantity of a binding inhibitor such as the above-mentioned 8-anilino-1-naphthalene sulphonic acid. The proteinaceous complex, the labeled ligand and the binding inhibitor may be combined in a 0.1 M sodium borate buffer at pH 8.4 which contains 0.1% of human serum albumin (fraction V), 0.1% of $NaN_3$ and which is 0.01 M in $Na_2$ EDTA. The reagent thus made can be pipetted into containers for storage. It will be understood, of course, that various other binding inhibitory agents could be employed as well. Such inhibitory agents include such sulphonic acid derivitives as 3-(4-anilino-1-naphthylazo)-2,7-naphthalene disulfonic acid, 2,4,6-trinitrobenzene sulphonic acid, and the like.

With respect to the reagent of the invention prepared specifically for the radioimmunoassay of $T_4$, the reagent has been found to be stable for periods of up to six weeks or more if stored at 4° C. in containers which exclude light, such as amber glass containers. Exposure to light degrades the 8-anilino-1-naphthalene sulphonic acid binding inhibitory agent.

The following example illustrates the preparation of a reagent of the invention as the same is applied to the radioimmunoassay of thyroxine.

EXAMPLE 1

Three solutions were made up as follows:

Solution A:

An aqueous solution was prepared which was 0.1 M in sodium borate (as a buffer - controlling pH to about 8.4) and which contained 0.5% bovine serum albumin, 0.1% $NaN_3$ and 5 mg/ml of 8-anilino-1-naphthalene sulfonic acid.

Solution B:

Into a one liter Erlenmeyer flask was placed 10.7 ml of normal rabbit serum, 17.2 ml of goat serum (containing goat antibody to rabbit immunoglobulins) and 280 ml of an aqueous potassium phosphate (0.01 M) buffer solution at pH 7.40 and containing 0.1% $NaN_3$, 0.01 M $Na_2$EDTA and 0.15 M NaCl. The resulting suspension was stirred at room temperature for one hour and then was stirred at 4° C. overnight. To the resulting suspension was added 2.0 ml of rabbit antiserum containing anti-$T_4$ antibody.

The resulting suspension was stirred at room temperature for two hours and was allowed to stand at 4° C. overnight. The flask was then centrifuged at approximately 4000 rcf for 15 minutes. The resulting precipitate was suspended in 500 ml of the above Solution A and was homogenized in a glass homogenizer with a Teflon pestle.

Solution C:

45.5 microliters of $^{125}I$-$T_4$ (at an activity of approximately 0.1 mCi/ml and a purity of approximately 90% as reported by the vendor, Amersham/Searle) were diluted to 20 ml with Solution A.

The reagent was prepared by combining 130 ml of Solution A, 50 ml of Solution B and 20 ml of Solution C. The mixture was stirred for 10 minutes and then was stored at 4° C. until needed.

The volumes of the immunoglobulins of this example were arrived at through titration to yield the maximum amount of precipitate.

To each of a series of test tubes containing 25 microliters of standard solutions of known $T_4$ concentrations (and also to test tubes containing 25 microliters of human serum substantially free of $T_4$) was added 1.0 ml of the reagent prepared above. No reagent was added to one of the tubes which contained the $T_4$-"free" human serum; instead, to that tube was added a reagent identical to that prepared as above but minus the anti-$T_4$ antibody. This tube was referred to as the "blank" tube. The other tube containing $T_4$-"free" serum and reagent was labeled the "zero binding" tube.

The tubes were incubated at 50° C. for one hour and then were centrifuged at 1500 rcf for 15 minutes. The supernatant was poured off and discarded, and the level of radioactivity was determined with a gamma counter.

The number of counts for each tube was then corrected by subtracting the average counts per minute of the blank tube from the average counts per minute of the other tubes. The amount of $^{125}I$-$T_4$ bound by the antibody complex as a percent of zero (termed $\%B_x/B_o$) was obtained by dividing the corrected sample counts by the corrected zero counts and multiplying by 100. On semilogarithmic graph paper, the quantity $\%B_x/B_o$ was plotted versus the respective $T_4$ concentrations, and a smooth line was drawn through the resulting points. It will be understood now that the compution of the value $\%B_x/B_o$ for a sample containing an unknown concentration of $T_4$ will permit one to derive the concentration of $T_4$ for that sample from the curve.

EXAMPLE 2

A reagent prepared generally in the manner set out above was employed to measure the concentration of $T_4$ in the blood serum of a patient. A series of test tubes were labeled A, B, C, D, and E and to each tube was added 20.0 microliters of calibration standards comprising human blood serum having 2.5, 5, 10, 20 and 40 micrograms per deciliter of $T_4$ respectively. 20 Microliters of patient blood serum was added to another tube. The tests were run in duplicate; that is, two tubes of each blood serum sample were employed. 1.0 Ml of the reagent was then pipetted into each of the tubes. The reagent was mixed thoroughly prior to pipetting and was maintained evenly suspended during the entire pipetting procedure. The tubes were then incubated at 50° C. for 30 minutes. 1.0 Ml of 0.9% normal saline (0.9% NaCl) was added to each of the tubes, which were then centrifuged at 1800 rcf for 20 minutes. Immediately after centrifugation, the supernatant from each tube was poured off, and the inverted tubes were blotted on absorbant paper and were then returned to upright positions. Each tube was then counted in a gamma counter, and the following results were obtained:

TABLE I

| Tube Label | Counts Per Minute | |
|---|---|---|
| | Tube #1 | Tube #2 |
| A | 56,479 | 55,797 |
| B | 50,934 | 49,404 |
| C | 38,974 | 39,536 |
| D | 30,755 | 29,704 |
| E | 22,642 | 21,769 |
| Unknown | 42,624 | 42,919 |

The counts thus measured for the tubes A, B, C, D, and E were plotted on semilogarithmic paper versus the known concentrations of $T_4$. The number of counts for the duplicate unknown patient samples were found on the curve to represent $T_4$ concentrations of 8.3 and 8.1 micrograms/deciliter, respectively, giving an average value of 8.2 micrograms per deciliter.

Essentially the same procedure may be used to determine the concentration of $T_3$ in blood serum. To increase the sensitivity of the $T_3$ determination, it is desirable to hold the samples at room temperature for an hour after incubation and before centrifugation.

The reagent of the invention is particularly desirable for measuring the concentration of ligands such as $T_3$, $T_4$, and the like which exchange readily with previously complexed ligands at temperatures of up to 50° or 56° C. Labeled ligands which are complexed with antibody sites can thus easily exchange with unlabeled ligands in the analytical procedure described above, with the result that substantial equilibrium is reached in a reasonably short period of time. Various ligands such as digoxin have been found to exchange slowly with previously complexed ligand, even at elevated temperatures. As a result, rather long periods of time are required for substantial equilibrium to be reached in this manner. Hence, it is desired that the reagent of the invention be particularly employed to measure the concentration of easily exchangeable ligands with which a substantial equilibrium can be achieved within about an hour at 56° C.

Manifestly, the instant invention provides a reagent and a method for its use which is simple, convenient, highly practical, and reliably accurate in the analysis of various ligands in human blood serum. The reagent is characterized, in its preferred embodiment, as being self-contained; that is, the reagent can be used without recourse to the use of additional reagents in an analytical procedure. The precipitate which is obtained in the analytical procedure is cohesive and is largely insensitive to physical manipulation which otherwise could cause a portion of the precipitate to be lost.

While a preferred embodiment of the present invention has been described, it should be understood that various changes, adaptations and modifications may be made therein without departing from the spirit of the invention and the scope of the appended claims.

What is claimed is:

1. Reagent for determining the concentration of a ligand in human blood serum and including a suspendable, water-insoluble, three-dimensional, proteinaceous complex which includes non-specific immunoglobulins, anti-ligand immunoglobulins, immunoglobulins which are antibodies to both the previously named immunoglobulins and which are complexed therewith to form said three-dimensional complex, and a labeled ligand complexed with the anti-ligand immunoglobulins, the complex being easily removed from suspension through centrifugation.

2. The reagent of claim 1 wherein the labeled ligand is $^{125}I$-$T_4$ or $^{125}I$-$T_3$.

3. The reagent of claim 1 wherein the labeled ligand is isotopically labeled cortisol.

4. The reagent of claim 1 including labeled ligand in excess of that complexed with the anti-ligand immunoglobulins.

5. The reagent of claim 2 including an aqueous carrier in which the proteinaceous complex is readily suspended, the carrier having a pH of at least about 8 and including a binding inhibitory agent preventing the binding of the ligand to thyroxine-binding globulin.

6. The reagent of claim 3 including an aqueous carrier in which the proteinaceous complex is readily suspended.

7. The reagent of claim 1 wherein the non-specific immunoglobulins are rabbit immunoglobulins.

8. The reagent of claim 1 wherein the anti-ligand immunoglobulins are anti-$T_4$ rabbit immunoglobulins.

9. The reagent of claim 1 wherein the anti-ligand immunoglobulins are anti-$T_3$ rabbit immunoglobulins.

10. The reagent of claim 1 wherein the immunoglobulins which are antibodies to the non-specific immunoglobulins and to the anti-ligand immunoglobulins are immunoglobulins raised in goats against rabbit immunoglobulins.

11. Reagent for determining the concentration of a ligand in human blood serum and including a readily suspendable, water-insoluble, three-dimensional, proteinaceous complex which includes nonspecific immunoglobulins from a given animal species and anti-ligand immunoglobulins raised in the same animal species, immunoglobulins raised in a different animal species and which are antibodies to both the previously named immunoglobulins and are complexed therewith to form said three-dimensional complex, and a labeled ligand complexed with the anti-ligand immunoglobulins, the labeled ligand being readily exchanged with unlabeled ligand so as to permit substantial equilibrium between labeled and unlabeled ligands to be reached within about one hour at 56° C.

12. In the method for the competitive binding assay of a ligand in human blood serum, the steps which comprise combining a measured quantity of human blood serum with a single, aqueous reagent which includes a suspendable, water-insoluble, three-dimensional, proteinaceous complex comprising non-specific immunoglobulins, anti-ligand immunoglobulins, immunoglobulins which are antibodies to both the previously named immunoglobulins and which are complexed therewith to form said three-dimensional complex, and a labeled ligand complexed with the anti-ligand immunoglobulins; and incubating the combined serum and reagent for not greater than about one hour at a temperature up to about 56° C. to permit substantial equilibrium between antibody-bound labeled and unlabeled ligands to be reached.

13. The method of claim 12 in which the ligand to be assayed is $T_4$, $T_3$, or cortisol.

14. The method of claim 13 including the steps of combining predetermined quantities of said reagent with standardized samples containing known concentrations of ligand and preparing a calibration curve in which, following attainment of substantial equilibrium between antibody-bound labeled and unlabeled ligands, values indicative of labeled or unlabeled ligand concentration are plotted against known concentrations of the ligand.

15. A method for preparing a liquid reagent for assaying the concentration of a ligand in human blood serum, comprising;
 (a) providing immunoglobulins from a first animal species which are anti-ligand antibodies;
 (b) providing immunoglobulins from a second animal species which are antibodies specific to immunoglobulins from the first animal species;
 (c) providing non-specific immunoglobulins from the first animal species;
 (d) reacting the non-specific immunoglobulins and the immunoglobulins from the second animal species to form an insoluble three-dimensional complex;
 (e) thereafter reacting the immunoglobulins which are anti-ligand antibodies with the complex to provide the complex with a plurality of available ligand binding sites; and
 (f) thereafter reacting the complex with labeled ligand in sufficient quantity so that a significant fraction of the binding sites are complexed with the labeled ligand.

16. The method of claim 15 in which the labeled ligand is provided in a quantity sufficient to provide unbound labeled ligand in the reagent.

17. The method of claim 15 including the subsequent step of dispensing the reagent into a storage container having walls less transmissive of light than clear glass.

* * * * *